United States Patent
Warm et al.

(10) Patent No.: US 8,439,902 B2
(45) Date of Patent: May 14, 2013

(54) APPARATUS AND METHOD FOR PROCESSING MATERIAL WITH FOCUSED ELECTROMAGNETIC RADIATION

(75) Inventors: Berndt Warm, Schwaig (DE); Peter Riedel, Nürnberg (DE); Claudia Gorschboth, Nürnberg (DE); Franziska Woittennek, Dresden (DE)

(73) Assignee: Wavelight GmbH, Erlangen (DE)

( * ) Notice: Subject to any disclaimer, the term of this patent is extended or adjusted under 35 U.S.C. 154(b) by 252 days.

(21) Appl. No.: 12/894,375

(22) Filed: Sep. 30, 2010

(65) Prior Publication Data
US 2012/0083771 A1 Apr. 5, 2012

(51) Int. Cl.
*A61B 18/18* (2006.01)
*A61N 5/00* (2006.01)

(52) U.S. Cl.
USPC ..... 606/10; 606/4; 606/5; 606/12; 250/492.1; 250/492.22

(58) Field of Classification Search .......... 606/4, 5, 606/10–12; 250/398, 492.1, 492.2–492.22; 128/898
See application file for complete search history.

(56) References Cited

U.S. PATENT DOCUMENTS

| | | | |
|---|---|---|---|
| 2006/0044510 A1* | 3/2006 | Williams et al. | 351/221 |
| 2009/0143772 A1* | 6/2009 | Kurtz | 606/4 |
| 2009/0171327 A1* | 7/2009 | Kurtz et al. | 606/6 |
| 2012/0130357 A1* | 5/2012 | Triebel et al. | 606/4 |

FOREIGN PATENT DOCUMENTS

| | | |
|---|---|---|
| DE | 102007060344 A1 | 6/2009 |
| DE | 102008015403 A1 | 9/2009 |
| WO | 2007096136 A1 | 8/2007 |

* cited by examiner

*Primary Examiner* — Ahmed Farah
(74) *Attorney, Agent, or Firm* — Keiko Ichiye

(57) ABSTRACT

An apparatus for processing material with focused electromagnetic radiation, comprises: a source emitting electromagnetic radiation, means for directing the radiation onto the material, means for focusing the radiation on or in the material, a unit for generating a pattern in the optical path of the electromagnetic radiation, an at least partially reflective surface in the optical path before the focus of the focused radiation, said pattern being imaged onto said at least partially reflective surface through at least part of said directing means and said focusing means, at least one detector onto which an image of the pattern is reflected by said surface and which generates electrical signals corresponding to said image, said image containing information on the position of the focus, a computer receiving said electrical signals and programmed to process said image so as to generate an electrical signal depending on the focal position, and a divergence adjustment element arranged in said optical path and adapted to receive said electrical signal of the computer so as to change a divergence of the electromagnetic radiation depending on said signal.

15 Claims, 2 Drawing Sheets

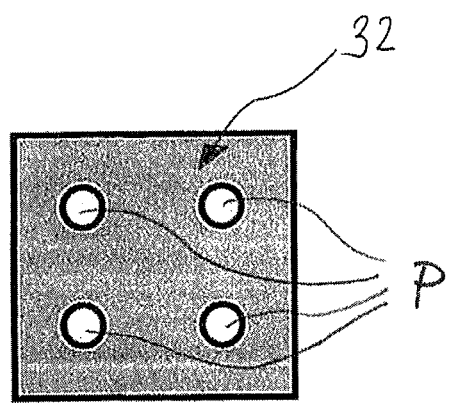
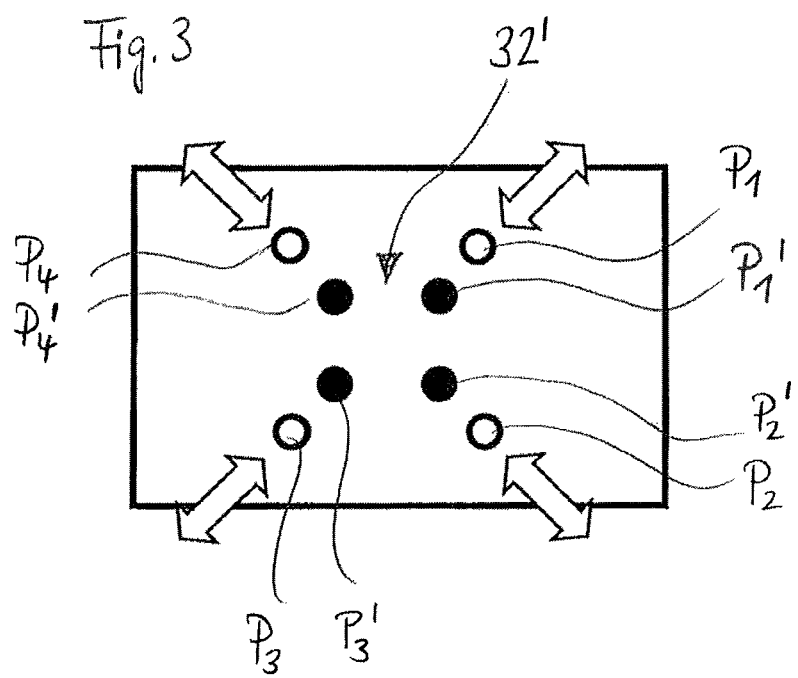

APPARATUS AND METHOD FOR PROCESSING MATERIAL WITH FOCUSED ELECTROMAGNETIC RADIATION

The invention relates to an apparatus and a method for processing material with focused electromagnetic radiation.

BACKGROUND OF THE INVENTION

The apparatuses in question are in particular optical systems directing electromagnetic radiation, generated e.g. by lasers or LEDs as radiation sources, onto or into a material to be processed, and forming and focusing said electromagnetic radiation. Material processing can here e.g. be a patterning of material in the micro-range of the type executed e.g. in semiconductors or also in metallic materials. The present invention can especially be used for ophthalmologic optical systems, in particular in refractive cornea surgery, such as LASIK.

When material is processed by means of focused electromagnetic radiation, it is normally of decisive importance to precisely position the focus, in particular in the direction of the electromagnetic radiation (normally referred to as "z-direction"). The position of the focus is normally referred to as "focal position". This term covers not only the above-explained location of the focus in the direction of the radiation (the so-called focus depth), but, more generally, also the position and the orientation of the focused radiation, i.e., by way of example, a displacement of the radiation with respect to the optical axis of the system or an angular position relative thereto.

US 2002/0171028 describes an apparatus for focus control, in which reflected light is made to interfere with a second beam through an optical imaging path, and an interferometric measurement and control are executed.

Also in U.S. Pat. No. 6,666,857 B2 focus control is executed by means of an interferometric wavefront control. Active wavefront control during photoablation on the human eye is accomplished by a combination of adaptive mirrors.

In US 2004/0021851 an optical array consisting of a laser and a subsequent beam shaping optics is used for measuring the focal length of an unknown lens. Measurement of the focal length is executed by focusing on a reference surface at different distances. The back-reflected part of the radiation is detected. The spot diameters are then evaluated with the respective distances. The focal length is determined by means of the "Newton" relation $Z Z'=f^2$. A diffraction grating, which is not described in detail, is used for outcoupling the back-reflected part of the radiation. Also the Jones matrix formalism is used for calculating the focal length. The method has a precision of 1%.

WO 2007/096136 A1 describes an apparatus for detecting the focal position of an optical system with a partially reflective surface on the focus to be measured, a camera for recording an image that is reflected by said surface, and a computer for evaluating the image recorded by the camera. An optical element is arranged in the optical path of the optical system before the focusing imaging system, said optical element influencing said image in accordance with the focal position. The focal position is controlled through elements of the focusing optics.

BRIEF SUMMARY OF THE INVENTION

In the following, the present invention will be described and explained especially with respect to the so-called fs-LASIK (femtosecond lasik), the use of the present invention in connection with other kinds of material processing, in the case of which an accurate control of the focal position is desired, resulting analogously.

It is an object of the present invention to allow in the processing of material with focused electromagnetic radiation a control, in particular a closed-loop control, of the focal position in a simple and reliable manner.

In one embodiment, the invention provides an apparatus for processing material with focused electromagnetic radiation, comprising:

a source of electromagnetic radiation, optical components for directing and focusing the radiation on or in the material, a unit for generating a pattern in the optical path of the electromagnetic radiation, an at least partially reflective surface in the optical path before the focus of the focused radiation, said pattern being imaged onto said at least partially reflective surface through at least part of said optical components, at least one detector onto which an image of the pattern is reflected by said surface and which generates electrical signals corresponding to said image, said image containing information on the position of the focus, a computer receiving said electrical signals and programmed to process said image so as to generate an electrical signal depending on the focal position, and a divergence adjustment element arranged in said optical path and adapted to receive said electrical signal of the computer so as to change a divergence of the electromagnetic radiation depending on said signal.

Making use of such an apparatus it is possible to control or control in a closed loop the focal position through the divergence adjustment element in that the computer derives the information on the focal position during image processing so as to generate, if the actual focal position should not correspond to a desired nominal focal position, a signal according to which the divergence adjustment element will change the beam divergence such that the actual focal position will correspond to the nominal focal position. A change in the beam divergence has the effect that the focal position will change without any necessity of actuating the focusing means (i.e. the focusing optics in the narrow sense of the term). If the beam divergence is increased, the focus will migrate in the direction of the beam, and if the beam divergence is reduced, the focus will migrate in a direction opposite to the beam direction.

According to a preferred embodiment of the present invention, said partially reflective surface is arranged at a location of the apparatus at which also the electromagnetic radiation exits the apparatus in the direction of the material to be processed.

Another preferred embodiment of the present invention is so conceived that the material to be processed is eye tissue, preferably the cornea. When the present invention is applied in this way, the apparatus is used for producing e.g. the so-called "flap", especially by means of a femtosecond laser. When the cornea is cut for producing the flap in fs-LASIK procedures, the cut has to be made, by controlling the focal position, in a particularly precise way and as planar as possible, i.e. the cut should be faithful to the focus depth. A glass plate is here typically pressed against the cornea with a so-called applanation surface so as to fix the eye and obtain a reference surface for cutting the flap in the stroma of the cornea. The focused pulses of the laser then cut in a depth of typically approx. 100 μm relative to the applanation surface a planar cut in the cornea. At the edge of the cut, the cutting depth is reduced so that the edge of the flap can be detached, with the exception of a "hinge", so that the flap can be clapped sideways.

The above-described invention allows an exact and unvarying adjustment of the cutting depth thus overcoming problems which occasionally arise in the prior art and which can originate from undesired variations of the cutting depth due to changes in the focal position occurring during the procedure in question. By means of the present invention, variations in the cutting depth can be reduced to a few μm.

In typical systems used nowadays for fs-LASIK, the cutting depth with respect to the so-called applanation surface, i.e. the surface with which the above-mentioned glass plate presses the cornea into a defined plane, is normally adjusted prior to the treatment by executing cuts on test specimens.

The present invention is based on the finding that, in spite of such a determination of the cutting depth with test specimens, undesirable variations of the preset cutting depths may nevertheless occur. Undesirable variations of the cutting depth may occur in the period of time between the determination of the cutting depth with respective test specimens as well as during surgery itself (i.e. during the execution of the cut), such undesirable variations being especially caused by

- a change in the divergence of the laser beam, especially due to thermal changes of the laser components or of other optical components, and also due to a drift of the laser beam direction,
- changes of the optical components used for focusing, again especially due to thermal changes, and
- manufacturing inaccuracies of the surfaces of the glass plate, which is pressed against the eye so as to define the applanation surface.

Once the cutting depth has been preset, making use of e.g. the above-mentioned test specimen, subsequent changes in the components, which influence the focal position, are no longer discerned and, in particular, no longer corrected in the prior art. The present invention overcomes this drawback and allows, selectively:

- recognition of changes in the laser beam divergence, caused in particular by thermal effects;
- recognition of changes in the focusing characteristics of the focusing optics, caused in particular by thermal effects;
- recognition of changes in the shape of the laser beam;
- recognition of changes in the beam direction;
- recognition of manufacturing inaccuracies with respect to the above-mentioned applanation surface and measurement of the same; and
- examination of the optical path up to a point directly before the material processing location, i.e. especially the cuts in fs-LASIK procedures; and, in addition,
- recognition of system faults in the laser or in the optical path, in particular during surgery.

Further preferred embodiments of the present invention are described in the dependent claims.

BRIEF DESCRIPTION OF THE DRAWINGS

In the following, embodiments of the present invention will be explained in more detail with reference to the drawing, in which:

FIG. 2 shows an embodiment for a mask in the optical path of the electromagnetic radiation; and FIG. 3 shows schematically the influence which changes in the beam divergence have on a pattern.

DETAILED DESCRIPTION OF PREFERRED EMBODIMENTS

Figure 1:
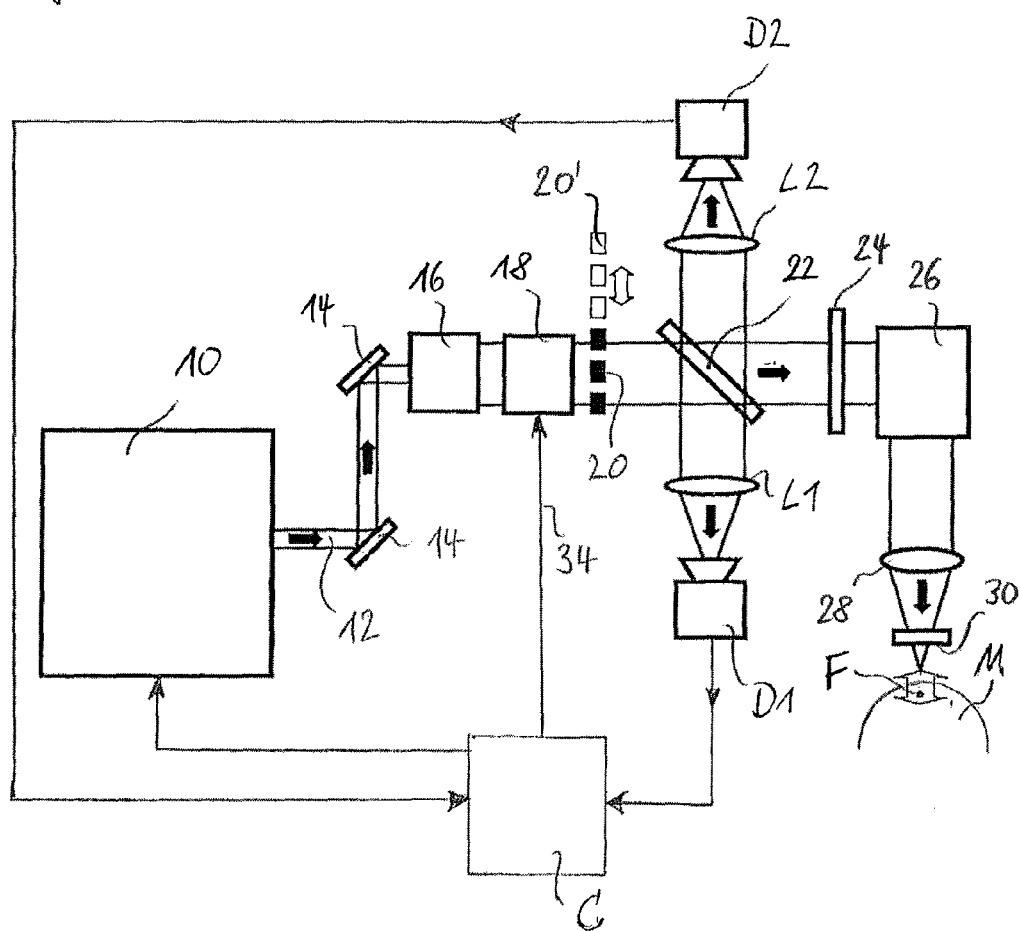
FIG. 1 shows schematically an apparatus for processing material with focused electromagnetic radiation.

The apparatus for processing material with focused electromagnetic radiation, which is shown in FIG. 1, concerns the cutting of a so-called flap in femtosecond lasik procedures, i.e. the production of a cut in the cornea of an eye representing here the material M.

A femtosecond laser of the type known for this kind of use serves as a radiation source 10. The radiation 12 emitted by the femtosecond laser is supplied via two deflection mirrors 14 to a beam expander 16 which expands the beam diameter. The expanded laser beam is directed into a divergence adjustment element 18, i.e. a unit by means of which the divergence of the laser beam can be increased or reduced. Components that can be used as a divergence adjustment element are especially a telescope with adjustable lenses, a system of deformable mirrors or deformable lenses. Subsequently, the laser beam passes through a pattern generator 20, e.g. a shadow mask of the type described in more detail hereinbelow. The pattern generator 20 produces an inhomogeneous distribution of the beam intensity across the cross-section of the beam. FIG. 2 shows exemplarily a shadow mask used for generating a pattern having four dots in the corners of a square. Also structures other than the holes shown are suitable for pattern generation. A variation of the divergence of the laser beam by means of the divergence adjustment element 18 causes a change in the dimensions of the mask images, i.e. the patterns, which are produced by the beam behind the mask. The pattern generator is preferably adapted to be swiveled into an out of the optical path.

After having passed the mask, the expanded laser beam, whose divergence has been adjusted, impinges on a beam splitter 22. A part of the beam is deflected by the beam splitter 22 in FIG. 1 downwards through a lens L1 onto a first detector D1. Another part of the laser beam passes rectilinearly through the beam splitter 22. This subbeam impinges on a shutter 24 and, if said shutter 24 is open, onto a deflection unit 26 by means of which the beam is guided and positioned relative to the eye M. A focusing optics is schematically represented by a lens 28. A glass plate is pressed against the cornea of the eye M with a (lower) applanation surface 30, as is common practice for cutting the flap in fs-LASIK procedures. The focus F of the laser beam is adjusted by the focusing optics (lens 28), and, during cutting of the flap, the focus is located in the cornea in a plane that is substantially perpendicular to the beam direction, e.g. at a depth of 100 μm relative to the surface of the cornea.

When the divergence of the laser beam is changed by means of the divergence adjustment element 18, the position of the focus F will change, as symbolized by the double arrow in FIG. 1, even if the other adjustments of the optical components remain unchanged.

The applanation surface 30 of the glass plate is partially reflective so that the image of the pattern generated by the pattern generator 20 on the applanation surface 30 is reflected back and is transmitted via the beam splitter 22 and a lens L2 to a second detector D2. The reflective applanation surface is located as close to the focus F as the material to be processed allows.

The two detectors D1, D2 are high-resolution electronic cameras and generate electrical signals from the images of the pattern produced by the pattern generator 20, which have been recorded by them, said electrical signals being transmitted to a computer C for image processing.

As a result of the function of the beam splitter 22, the first detector D1 receives pattern images which are transmitted from the radiation source 10 to the first detector D1 without having been reflected on the partially reflective surface 30. The second detector D2 receives pattern images which are reflected back from the partially reflective surface 30. The lenses L1 and L2 format the images on the detectors so as to accomplish the maximum resolution.

Due to the above-described arrangement of the optical components with respect to the detectors D1 and D2, the pattern images received by the detectors contain information on the optical condition of all the optical components of the apparatus, in particular information on the divergence of the beam, when said beam passes through the pattern generator 20. The first detector D1 detects this information for the optical path before the beam splitter 22, and the second detector D2 detects this information with respect to all the components in the optical path from the source 10 to the applanation surface 30.

The pattern generator 20 can e.g. be configured as a plate with holes (shadow mask) that is adapted to be inserted in the optical path. The fact that the shadow mask is displaceable is indicated in FIG. 1 by the double arrow, and the position at which the shadow mask is removed from the optical path is designated by reference numeral 20'.

Instead of the shadow mask, also electro-optical means may be provided, which remain in the optical path and which can be controlled such that they allow, selectively, free passage of the beam or the formation of a mask in the optical path, said mask being used for generating a pattern.

The function of the apparatus according to FIG. 1 for effecting control or closed-loop control of the position of the focus F is as follows:

As has been explained at the beginning, undesirable displacements of the focal position may occur in apparatuses of the type in question due to changes in the optical characteristics of components in the optical path of the radiation emitted by the source 10, said changes being especially caused by thermal effects. A change in the focal position occurs in particular when the beam divergence changes. When the divergence of the laser beam changes, the images of the mask (i.e. the images of the pattern produced by the mask) on the detectors D1, D2 will become larger or smaller, depending on whether the divergence increases or decreases. Characteristics of the image, in particular the size of the mask image formed on the applanation surface 30, are also a measure of the focal position, i.e. the radiation pattern image formed on the applanation surface contains information on the position of the focus F, the radiation pattern being generated by the pattern generator 20. The image processing means in the computer C can use this information for computing control signals for the divergence adjustment element 18, which are used for controlling the divergence of the beam such that the focus F will have a desired position.

FIG. 2 shows an example of a shadow mask having four dots P. FIG. 3 shows how the image of this shadow mask on the applanation surface 30 may change in dependence upon varying divergences of the radiation. These changes are marked e.g. by the double arrows in FIG. 3. For example, when the divergence changes symmetrically, the original positions of the dots P1, P2, P3, P4 can migrate inwards to the respective positions P1', P2', P3' and P4', which means that the focus F will approach the applanation surface 30. If the desired focal position corresponds, however, to the original position of the dots P1, P2, P3 and P4, this original position can be re-established by changing the divergence (e.g. by increasing the divergence depending on the nature of the optical components). This can be executed after the fashion of a closed loop, so that in the period of time between preparatory surgery measures, e.g. an optical calibration of the system, and the end of surgery the desired focus depth will always be maintained with high accuracy.

From the above it can be seen that the image of the mask on the surface 30 contains information on the position of the focus F. It can also be seen that the image of the pattern on said surface can be changed by adjusting the divergence by means of a divergence adjustment element 18.

Making use of these functional dependencies, it is possible to calibrate the optical apparatus according to FIG. 1 with respect to the focal position, i.e. to experimentally assign to each focal position an image on the surface 30 in the variation ranges to be expected using a test eye or the like. This image is then recorded by the detector D2 and stored in the computer C together with data, e.g. the focus depth, characterizing the focal position. For the purpose of image processing, the computer C can have stored therein data which are acquired experimentally (empirically) in that specific focal positions are assigned to respective pattern images. This functional assignment can be executed e.g. in tabular form or by an empirically obtained mathematical function. For the given optical system of the apparatus, changes in the image sizes of the pattern are an unequivocal function of changes in the divergence of the radiation and, in addition, changes in the focal position are also an unequivocal function of the change in image sizes and, consequently, an unequivocal function of changes in divergence. These functional dependencies can be ascertained empirically for a given optical system, i.e. an apparatus according to FIG. 1, in advance, and stored in the computer C in the way described.

In the closed loop, the divergence adjustment element 18 acts as an adjustment element. The disturbance variable of the closed loop is determined on the basis of the detector images. For example, length information (dimensions), e.g. dimensions between the dots according to FIG. 3, can be obtained from the image of the mask. Through interpolation the magnitudes used as a basis for the analysis can be more accurate than pixel dimensions of the detectors D1, D2.

According to FIG. 3, for example, the distance between the solid dots and the empty dots can be ascertained in the computer C by image processing, and an empirically obtained function, which comprises the change in the distances in response to a change in the focal position, can be used for reestablishing, through a change in divergence caused by means of the divergence adjustment element 18, the position of the dots calculated from the stored functions, and, consequently, the desired focal position. This is all done relatively with reference to an initially experimentally (empirically) ascertained reference situation in which the focal position is measured on the basis of e.g. a test eye or the like and in which this focal position represents e.g. precisely the desired cutting depth for cutting a flap in the fs-LASIK procedure. This desired reference depth has then associated therewith very specific dimensions of the dots in the pattern image according to FIGS. 2 and 3, and the computer C controls the divergence adjustment element 18 such that the dot distances corresponding to the desired focal position will be maintained before and during surgery.

Disturbance variables are especially thermal changes in the optical wavelength on the path of the radiation from the source 10 to the beam splitter 22, changes in divergence along this path or also other changes of the optical components. This leads to changes in the images on both detectors D1, D2, the change on detector D1 containing already all the information on these disturbance variables.

Changes of the optical components occurring along the path from the beam splitter 22 to the applanation surface 30, in particular thermally conditioned changes, or also an incorrect positioning of the applanation surface 30 lead to changes in the image on the detector D2, without any influence on the images recorded by detector D1.

This means that the computer can also be used for evaluating the disturbance variables, and the disturbances can possibly be localized, i.e. associated with specific optical components.

The above-described system allows, in addition to the above-described control of the focal position, also monitoring of the system in other essential respects under the aspect of increased operational reliability. For example, a monitoring function can be implemented by means of the computer for detecting beam interruptions, changes in beam ellipticity, contaminations, defects of the optical system, etc. All this affects the pattern image appearing on one of the two detectors D1, D2, and can be evaluated so as to exclude any risk for the patient, e.g. when surgery has to be discontinued due to the fact that the above-mentioned parameters deviate from predetermined nominal values.

In order to limit the computational effort required for image processing in the computer C as far as possible, it will be advisable to choose the simplest possible version of the pattern produced by the pattern generator 20. This can be accomplished by making use of the comparatively simple mask shown in FIG. 2. On the basis of the array of dots shown, respective one-dimensional distributions with two peaks each can be produced by summing up columns and rows. The distance between these peaks can be determined without major computing effort with local resolutions better than a pixel distance (by interpolation).

Shadow masks can be realized e.g. by providing holes in metal plates, blackened films, holographic elements, lens arrays, etc. Simple masks can be processed by image processing without major computational effort and almost in real time, whereas more complex masks allow a larger number of controlling functions and error analyses.

As a modification of the embodiment described hereinbefore with respect to FIG. 1, it is possible to omit the detector D1 and the associated lens L1 or to replace it by a mirror. When the detector D1 is replaced by a mirror, a beam deflection can be added, which either allows the beam to pass to the focus F or blocks it towards the mirror.

Another modification of the embodiment according to FIG. 1 can be so conceived that the detector D2 and the associated lens L2 are omitted or replaced by a mirror. If the shutter 24 is closed, this will allow the measurement of the beam distribution of the exiting beam. If the shutter 24 is open, the image distribution, which is already present on the detector D1, will be superimposed by a second beam distribution (reflected by the surface 30). The two images can be processed relative to one another; one image can, for example, be subtracted from the other. In so doing, the two images can be spatially separated from one another, whereby image processing will be simplified.

If the detector D1 and the associated lens L1 are omitted, the shutter 24 can be replaced by a swiveling mirror so as to record, with a time shift and depending on the angular condition of the mirror, the images which are here of interest with only one detector D2 (camera).

Instead of using two-dimensional cameras as detectors, it is also possible to use line scan cameras for this purpose, when line patterns are predetermined for the pattern generator.

Likewise, the focal position can be controlled, with regard to its position and its angle, by a configuration of the deflection mirrors 14. Also the focus position, i.e. the location of the focus in a plane extending perpendicular to the beam direction, has an influence on the image of the pattern on the applanation surface 30 and can, by image processing in the computer C, be used for controlling the focus position by means of the deflection mirrors, which are implemented as motor-adjustable elements controllable by the computer C. To this end, the computer C can, analogously to that which has been explained hereinbefore on the basis of the focus depth in connection with the divergence, also be programmed empirically (experimentally) such that it will control the deflection mirrors 14 in such a way that the focus position will be adjusted at right angles to the beam direction to a desired value predetermined by the computer. This desired position of the focus is maintained during cutting of a flap in the plane defined by the constant focus depth.

The above applies in a corresponding manner also to the direction of the radiation at the location of the focus F, which also finds expression in the image of the pattern on the surface 30 and which can therefore be subjected to control and closed-loop control, analogously to the statements made hereinbefore with respect to the connection between focus depth and divergence, by controlling the deflection mirrors 14 by means of the computer C.

The invention claimed is:

1. An apparatus for processing material with focused electromagnetic radiation, comprising:
   a source of the electromagnetic radiation,
   a plurality of optical components arranged to direct and focus the radiation at a focus on or in the material,
   a unit configured to generate a pattern in the optical path of the electromagnetic radiation,
   an at least partially reflective surface in the optical path located before the focus of the focused radiation, said pattern being imaged onto said at least partially reflective surface through at least part of said optical components,
   at least one detector configured to detect an image of the pattern reflected by said surface and to generate one or more electrical signals in response to detecting said image, said image containing information on the position of the focus,
   a computer receiving said electrical signals and programmed to determine from the image if there is a change in the pattern indicating a change in the focus from an original position and to generate a control signal to change a divergence of the electromagnetic radiation to reestablish the original position if there is a change in the pattern, and
   a divergence adjustment element arranged in said optical path and adapted to receive said control signal to change the divergence of the electromagnetic radiation to reestablish the original position.

2. An apparatus according to claim 1, wherein said surface is arranged at the location where the electromagnetic radiation exits the apparatus.

3. An apparatus according to claim 1, wherein the material is a cornea of an eye.

4. An apparatus according to claim 1, wherein the source is a femtosecond laser.

5. An apparatus according to claim 1, wherein said surface is an applanation surface adapted to be pressed against a cornea.

6. An apparatus according to claim 1, wherein the pattern comprises two or more dots.

7. An apparatus according to claim 1, wherein the divergence adjustment element comprises one of a telescope, a deformable mirror, and a deformable lens.

8. An apparatus according to claim 1, wherein the at least one detector includes at least two detectors, one of said detectors detecting radiation emitted by the source, and the other of said detectors detecting radiation reflected by the surface.

9. An apparatus according to claim 1, wherein the unit generating the pattern is disposed in the optical path of the electromagnetic radiation after the divergence adjustment element.

10. An apparatus according to claim 1, wherein the pattern comprises a plurality of dots arranged in a matrix.

11. An apparatus according to claim 1, wherein the change in the pattern is a change in the size of the pattern 12. A method for processing material with focused electromagnetic radiation, comprising:
    generating the electromagnetic radiation by a source,
    directing the radiation onto the material to be processed,
    focusing the radiation at a focus on or in the material,
    generating a pattern in the optical path of the electromagnetic radiation,
    providing an at least partially reflective surface in the optical path of the electromagnetic radiation before the focus of the focused radiation,
    imaging said pattern on said at least partially reflective surface,
    detecting, by at least one detector, an image of the pattern reflected by said surface, the detected image containing information on the position of the focus,
    generating one or more electrical signals in response to detecting the image,
    processing said electrical signals in a computer to determine from the image if there is a change in the pattern indicating a change in the focus from an original position and to generate a control signal to change a divergence of the electromagnetic radiation to reestablish the original position if there is a change in the pattern, and
    adjusting the divergence of said electromagnetic radiation depending on said control signal to reestablish the original position.

13. A method according to claim 12, wherein said surface is an applanation surface adapted to be pressed against a cornea 14. A method according to claim 12, wherein the pattern comprises a plurality of dots arranged in a matrix.

15. A method according to claim 12, wherein the change in the pattern is a change in the size of the pattern.

* * * * *